United States Patent [19]

Petusky

[11] Plant 5,052

[45] May 10, 1983

[54] CHRYSANTHEMUM NAMED SUNLIGHT

[76] Inventor: Kerry S. Petusky, 28 W 748 Barnes Ave., West Chicago, Ill. 60185

[21] Appl. No.: 315,914

[22] Filed: Oct. 28, 1981

[51] Int. Cl.[3] ..... A01H 5/00

[52] U.S. Cl. ..... Plt./74

[58] Field of Search ..... Plt./74

*Primary Examiner*—Robert E. Bagwill

[57] ABSTRACT

A new cultivar of chrysanthemum particularly suitable for four-inch and six-inch pot plant production, characterized by its single flower form of medium size and yellow coloration, its abundant production of blooms when grown as a spray pot, its abundant pollen production, its nine-week photoperiodic response, and its ability for year around flowering on medium treatment.

1 Drawing Figure

BACKGROUND OF THE NEW PLANT

My new variety of pot chrysanthemum was selected by me from a population of seedlings resulting from the hybridization of the variety 'Improved Yellow Bonnie Jean' (U.S. Plant Pat. No. 3,404) with the variety 'Fiesta' (U.S. Plant Pat. No. 3,632) with the objective of creating new and unusual varieties. This hybridization was performed by me during March 1976, seeds were then harvested and sown and flowered October 1976. From this population of flowering seedlings, this new plant was selected by me and asexually reproduced under my direction and further propagated by means of vegetative cuttings. This work was performed in greenhouses at West Chicago, Ill.

Through successive generations of asexual reproduction, this plant has proved that its distinctive characteristics are firmly fixed and hold true from generation to generation.

DESCRIPTION OF THE DRAWINGS

My new chrysanthemum variety is illustrated by the accompanying drawings which is a full color photographic rendition showing the new variety as it appears as a fully grown potted plant.

DESCRIPTION OF THE NEW PLANT

The following is a detailed description of my new variety of chrysanthemum, the color designations being according to The R.H.S. Colour Chart published by The Royal Horticultural Society of London, England.

THE PLANT

Origin: Seedling.

Parentage: Improved Yellow Bonnie Jean (U.S. Plant Pat. No. 3,404)×Fiesta (U.S. Plant Pat. No. 3,632).

Classification:

*Botanic.*—*Chrysanthemum morifolium.*

*Commercial.*—Greenhouse pot plant.

Form: Vase-shaped, perennial herbaceous bush.

Height: Varies with cultural practices.

Growth: Upright and vigorous, sturdy, with very good strength.

Branching: Normal under natural conditions.

Foliage:

*Quantity.*—Abundant, 7 to 10 leaves on 8 cm. stem.

*Leaf size.*—Length — Approximately 8.4 to 10.6 cm. (typical mature leaf). Width — Approximately 4.2 to 6.5 cm. (typical mature leaf).

*Shape.*—Lobed, deeply serrated.

*Texture.*—Canescent.

*Color.*—Upper side — 139A. Under side — 137B.

*Venation.*—Pinnate.

*Petioles.*—Length — Approximately 0.9 to 2.3 cm.

THE BUD

Form: Globular.

Size: Varies in both diameter and depth.

Opening rate: Slow, typical chrysanthemum.

Color:

*When phyllaries first divide.*—8A, 10A.

*When florets begin to unfurl.*—12A, 12B.

Phyllaries: Many involucral, upstanding bracts on the outside of the receptacle.

*Shape.*—Spear-shaped.

*Color.*—Inside — 138A. Outside — 137B.

*Surface texture.*—Pubescent.

Peduncle: Sturdy and erect.

*Length.*—Varies considerably.

*Surface texture.*—Canescent.

*Color.*—148B.

THE FLOWER

Response: 9 week.

Recommended flowering: Year around with photoperiodic control.

Blooms:

*Type.*—Single and composite.

*Borne.*—A head of many florets borne on a receptacle.

*Shape.*—Cup-shaped.

*Size.*—Medium-size bloom. Diameter — Approximately 6.0 to 6.8 cm. Depth — Approximately 1.5 to 2.3 cm.

Florets:

*Quantity.*—Numerous.

*Form.*—Linear with obtuse apex.

*Firmness.*—Medium to medium-soft.

*Appearance.*—Very slight shine.

*Color.*—Ray florets — Upper side: 5A, 6A, 6B, 7C. Reverse side: 6D, 7D. Disc florets — 6A. Discoloration — Very slight fade as full bloom ages.

Persistence: Flowers hang on and dry.

Lasting quality:

*On plant.*—4 weeks. Not recommended for cut-flower use.

REPRODUCTIVE ORGANS

Stamens:

*Quantity.*—5 to each disc floret.

*Arrangement.*—Syngenesious.

*Filaments.* —Length — 2 to 4 mm. Color — yellow.

*Pollen.*—Color — yellow.

Pistils:

*Number.*—One to each ray and disc floret.

*Styles.*—Length — 4 to 5 mm.

*Stigmas.*—Color — yellowish-green.

Ovaries: Inferior bicarpellate.

This new variety of chrysanthemum is particularly characterized by its single flower form with clear, medium yellow ray florets which do not reflex upon maturation and disc florets which are initially greenish-yellow, gradually becoming more yellow as the bloom matures. Disc florets produce abundant pollen.

This plant is also characterized by its spreading pot habit, its abundant, dark green foliage, its very abundant production of blooms when grown as a spray pot, and its ability to be flowered year around, the plant flowering approximately nine weeks from the commencement of short-day treatment.

Because of its medium growth rate and spreading habit, it is particularly suitable for four-inch and six-inch, medium treatment pot production.

I claim:

1. A new and distinctive cultivar of chrysanthemum, substantially and herein shown and described, particularly characterized by its single flower form, medium flower size, yellow coloration of the ray florets, greenish-yellow coloration of the disc florets, very floriferous habit and its applicability for four and six-inch pot production.

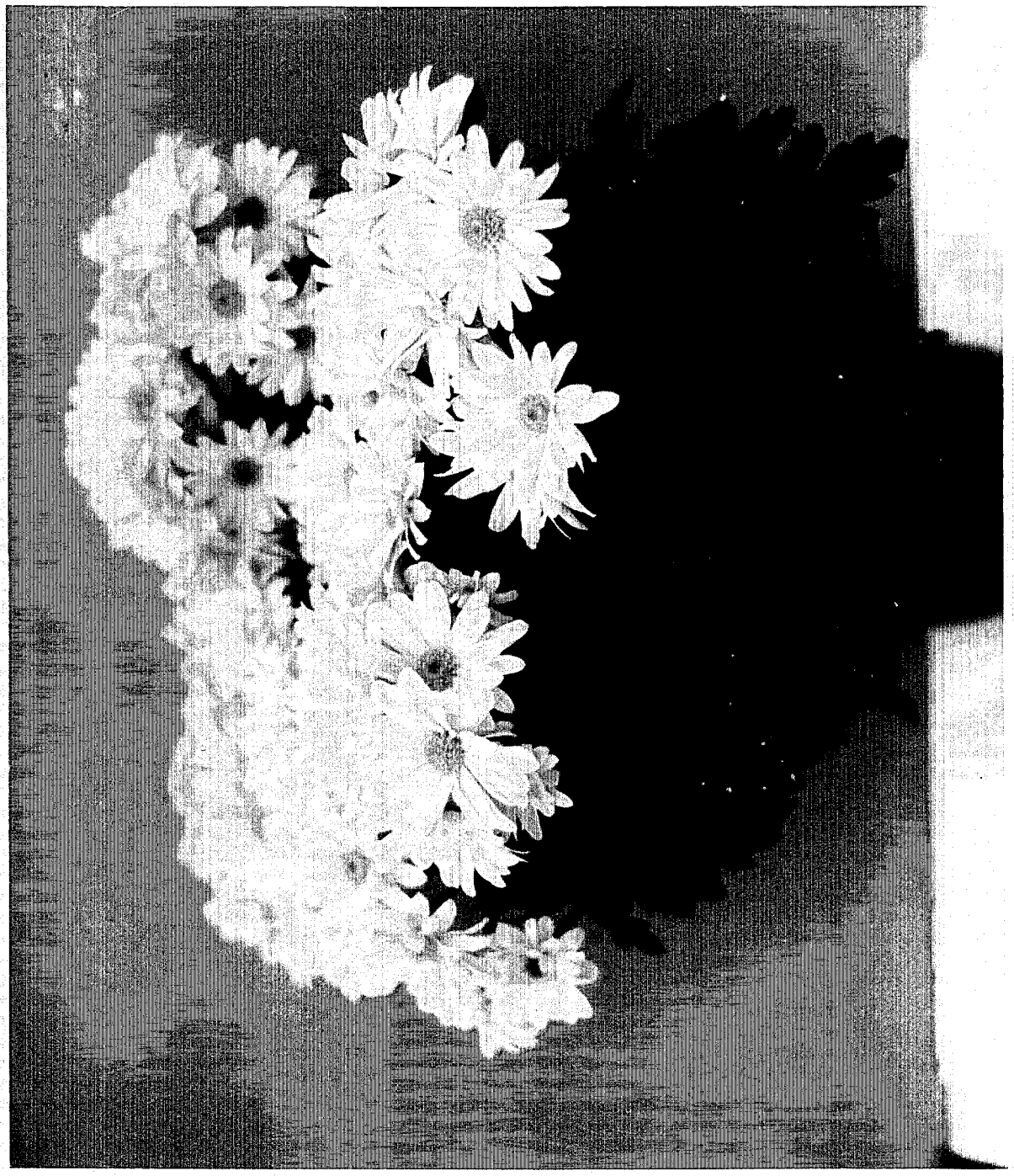

* * * * *